(12) United States Patent
Hestad et al.

(10) Patent No.: US 8,372,131 B2
(45) Date of Patent: Feb. 12, 2013

(54) SURGICAL SITE ACCESS SYSTEM AND DEPLOYMENT DEVICE FOR SAME

(75) Inventors: Hugh D. Hestad, Edina, MN (US); Zachary M. Hoffman, Bloomington, MN (US); Robert G. Hudgins, Burnsville, MN (US); John T. Maertens, Chaska, MN (US); Thomas O. Viker, Arden Hills, MN (US)

(73) Assignee: Power Ten, LLC

( * ) Notice: Subject to any disclaimer, the term of this patent is extended or adjusted under 35 U.S.C. 154(b) by 364 days.

(21) Appl. No.: 11/778,125

(22) Filed: Jul. 16, 2007

(65) Prior Publication Data
US 2009/0024203 A1 Jan. 22, 2009

(51) Int. Cl.
*A61F 2/06* (2006.01)
(52) U.S. Cl. ...... 623/1.11; 623/1.12; 623/1.2; 623/1.23; 606/108; 606/185; 606/191
(58) Field of Classification Search .................. 623/1.12, 623/1.14, 1.2, 1.23, 1.11, 1.15, 1.13, 17.11–17.16; 600/201, 208; 606/198, 1, 2, 15, 14, 16, 606/99, 167, 108, 185; 604/164.08, 164.11, 604/104, 164.1
See application file for complete search history.

(56) References Cited

U.S. PATENT DOCUMENTS

| | | | |
|---|---|---|---|
| 4,655,771 A | 4/1987 | Wallsten | |
| 5,035,706 A * | 7/1991 | Giantureo et al. | 606/198 |
| 5,163,949 A | 11/1992 | Bonutti | |
| 5,197,971 A | 3/1993 | Bonutti | |
| 5,295,994 A | 3/1994 | Bonutti | |
| 5,320,611 A | 6/1994 | Bonutti et al. | |
| 5,331,975 A | 7/1994 | Bonutti | |
| 5,345,927 A | 9/1994 | Bonutti | |
| 5,431,676 A | 7/1995 | Dubrul et al. | |
| 5,454,365 A | 10/1995 | Bonutti | |
| 5,460,170 A * | 10/1995 | Hammerslag | 600/201 |
| 5,514,153 A | 5/1996 | Bonutti | |
| 5,573,517 A | 11/1996 | Bonutti et al. | |
| 5,575,517 A | 11/1996 | Thomas | |
| 5,601,590 A | 2/1997 | Bonutti et al. | |
| 5,658,272 A | 8/1997 | Hasson | |
| 5,667,520 A | 9/1997 | Bonutti | |
| 5,674,240 A | 10/1997 | Bonutti et al. | |
| 5,685,286 A | 11/1997 | Summers | |
| 5,707,390 A | 1/1998 | Bonutti | |
| 5,741,326 A * | 4/1998 | Solovay | 623/2.25 |

(Continued)

FOREIGN PATENT DOCUMENTS

| | | |
|---|---|---|
| AU | 5621198 | 7/1998 |
| GB | 2428198 A | 1/2007 |

(Continued)

*Primary Examiner* — Ryan Severson
*Assistant Examiner* — Tin Nguyen
(74) *Attorney, Agent, or Firm* — Jennifer Meredith, Esq.; Lippes Mathias Wexler Friedman LLP (57) ABSTRACT

An expandable surgical site access system and method for using the expandable surgical site access system to perform minimally invasive, percutaneous surgeries to access the spine or other bone structures, organs, or locations of the body is disclosed. In one embodiment, the surgical site access system includes an elongated, expandable stent that is particularly adapted to be deployed in a body during a surgical procedure to provide access to a surgical site within the body. The stent defines a working channel through the body from a point of entry to the surgical site.

11 Claims, 12 Drawing Sheets

U.S. PATENT DOCUMENTS

| | | | |
|---|---|---|---|
| 5,792,044 | A | 8/1998 | Foley et al. |
| 5,814,058 | A | 9/1998 | Carlson |
| 5,827,227 | A | 10/1998 | Delago |
| 5,827,318 | A | 10/1998 | Bonutti |
| 5,827,319 | A | 10/1998 | Carlson et al. |
| 5,860,997 | A | 1/1999 | Bonutti |
| 5,888,196 | A | 3/1999 | Bonutti |
| 5,954,739 | A | 9/1999 | Bonutti |
| 5,961,499 | A | 10/1999 | Bonutti |
| 5,997,508 | A | 12/1999 | Lunn |
| 5,997,570 | A | 12/1999 | Ligtenberg |
| 6,042,596 | A | 3/2000 | Bonutti |
| 6,102,928 | A | 8/2000 | Bonutti |
| 6,126,685 | A | 10/2000 | Lenker et al. |
| 6,165,210 | A | 12/2000 | Lau et al. |
| 6,171,282 | B1 | 1/2001 | Ragsdale |
| 6,171,299 | B1 | 1/2001 | Bonutti |
| 6,187,023 | B1 | 2/2001 | Bonutti |
| 6,217,509 | B1 | 4/2001 | Foley et al. |
| 6,277,136 | B1 | 8/2001 | Bonutti |
| 6,282,068 | B1 | 8/2001 | Pinarbasi |
| 6,338,730 | B1 | 1/2002 | Bonutti et al. |
| 6,358,266 | B1 | 3/2002 | Bonutti |
| 6,451,042 | B1 | 9/2002 | Bonutti |
| 6,530,926 | B1 | 3/2003 | Davison |
| 6,613,038 | B2 | 9/2003 | Bonutti et al. |
| 6,620,181 | B1 | 9/2003 | Bonutti |
| 6,719,934 | B2 | 4/2004 | Stinson |
| 6,800,084 | B2 | 10/2004 | Davison et al. |
| 6,811,546 | B1 | 11/2004 | Callas et al. |
| 6,811,558 | B2 | 11/2004 | Davison et al. |
| 6,814,715 | B2 | 11/2004 | Bonutti et al. |
| 6,837,891 | B2 | 1/2005 | Davison et al. |
| 6,849,064 | B2 | 2/2005 | Hamada |
| 6,858,034 | B1 | 2/2005 | Hijlkema et al. |
| 6,972,026 | B1 | 12/2005 | Caldwell et al. |
| 7,001,397 | B2 | 2/2006 | Davison et al. |
| 7,033,369 | B2 | 4/2006 | Davison et al. |
| 7,108,705 | B2 | 9/2006 | Davison et al. |
| 7,179,225 | B2 | 2/2007 | Shluzas et al. |
| 7,217,273 | B2 | 5/2007 | Bonutti |
| 2001/0011170 | A1 | 8/2001 | Davison et al. |
| 2002/0013601 | A1 | 1/2002 | Nobles et al. |
| 2002/0035373 | A1 | 3/2002 | Carlson et al. |
| 2002/0062148 | A1 | 5/2002 | Hart |
| 2002/0095160 | A1 | 7/2002 | Bonutti |
| 2003/0009130 | A1 | 1/2003 | Stecker et al. |
| 2003/0014068 | A1 | 1/2003 | Bonutti et al. |
| 2003/0023260 | A1 | 1/2003 | Bonutti |
| 2003/0032975 | A1 | 2/2003 | Bonutti |
| 2003/0074045 | A1* | 4/2003 | Buzzard et al. ............... 623/1.11 |
| 2003/0181939 | A1 | 9/2003 | Bonutti |
| 2003/0195493 | A1 | 10/2003 | Davison et al. |
| 2003/0195549 | A1 | 10/2003 | Davison et al. |
| 2003/0195550 | A1 | 10/2003 | Davison et al. |
| 2003/0195551 | A1 | 10/2003 | Davison et al. |
| 2003/0199884 | A1 | 10/2003 | Davison et al. |
| 2003/0199885 | A1 | 10/2003 | Davison et al. |
| 2003/0209835 | A1 | 11/2003 | Chun |
| 2003/0216770 | A1* | 11/2003 | Persidsky et al. ............. 606/191 |
| 2004/0006344 | A1 | 1/2004 | Nguyen et al. |
| 2004/0078051 | A1 | 4/2004 | Davison et al. |
| 2004/0093001 | A1 | 5/2004 | Hamada |
| 2004/0093002 | A1 | 5/2004 | Davison et al. |
| 2004/0097949 | A1 | 5/2004 | Bonutti |
| 2004/0098012 | A1 | 5/2004 | Davison et al. |
| 2004/0098016 | A1 | 5/2004 | Bonutti |
| 2004/0098095 | A1 | 5/2004 | Burnside |
| 2004/0127912 | A1 | 7/2004 | Rabkin et al. |
| 2004/0127930 | A1 | 7/2004 | Bonutti |
| 2004/0133201 | A1 | 7/2004 | Shluzas et al. |
| 2004/0138689 | A1 | 7/2004 | Bonutti |
| 2004/0143285 | A1 | 7/2004 | Bonutti |
| 2004/0193181 | A1 | 9/2004 | Bonutti |
| 2004/0236404 | A1 | 11/2004 | Penn et al. |
| 2005/0043754 | A1 | 2/2005 | Davison et al. |
| 2005/0049672 | A1 | 3/2005 | Murphy |
| 2005/0075540 | A1 | 4/2005 | Shluzas et al. |
| 2005/0090822 | A1 | 4/2005 | DiPoto |
| 2005/0090833 | A1 | 4/2005 | DiPoto |
| 2005/0090899 | A1 | 4/2005 | DiPoto |
| 2005/0119685 | A1 | 6/2005 | Smith |
| 2005/0124937 | A1 | 6/2005 | Kick et al. |
| 2005/0125021 | A1 | 6/2005 | Nance et al. |
| 2005/0165432 | A1 | 7/2005 | Heinrich |
| 2005/0180919 | A1 | 8/2005 | Tedeschi |
| 2005/0182436 | A1* | 8/2005 | Chopra ........................ 606/192 |
| 2005/0203565 | A1 | 9/2005 | Rethy et al. |
| 2005/0209627 | A1 | 9/2005 | Kick et al. |
| 2005/0240209 | A1 | 10/2005 | Hamada |
| 2005/0241647 | A1 | 11/2005 | Nguyen et al. |
| 2005/0245942 | A1 | 11/2005 | DiPoto |
| 2005/0245960 | A1 | 11/2005 | Grundeman |
| 2005/0251192 | A1 | 11/2005 | Shluzas et al. |
| 2005/0273131 | A1 | 12/2005 | Shluzas et al. |
| 2005/0273132 | A1 | 12/2005 | Shluzas et al. |
| 2005/0273133 | A1 | 12/2005 | Shluzas et al. |
| 2006/0004401 | A1 | 1/2006 | Abernathie et al. |
| 2006/0036276 | A1 | 2/2006 | Nguyen et al. |
| 2006/0041270 | A1 | 2/2006 | Lenker et al. |
| 2006/0069404 | A1 | 3/2006 | Shluzas et al. |
| 2006/0089662 | A1 | 4/2006 | Davison et al. |
| 2006/0106416 | A1 | 5/2006 | Raymond et al. |
| 2006/0142795 | A1 | 6/2006 | Nguyen et al. |
| 2006/0149136 | A1 | 7/2006 | Seto et al. |
| 2006/0167487 | A1 | 7/2006 | Hamada |
| 2006/0178693 | A1 | 8/2006 | Hamada |
| 2006/0195017 | A1 | 8/2006 | Shluzas et al. |
| 2006/0200185 | A1 | 9/2006 | Marchek et al. |
| 2006/0200186 | A1 | 9/2006 | Marchek et al. |
| 2006/0200188 | A1 | 9/2006 | Nance et al. |
| 2006/0200189 | A1 | 9/2006 | Nance et al. |
| 2006/0212062 | A1 | 9/2006 | Farascioni |
| 2006/0229501 | A1 | 10/2006 | Jensen et al. |
| 2006/0241671 | A1 | 10/2006 | Greenhalgh |
| 2006/0247500 | A1 | 11/2006 | Voegele et al. |
| 2006/0247516 | A1 | 11/2006 | Hess et al. |
| 2006/0247586 | A1 | 11/2006 | Voegele et al. |
| 2006/0247673 | A1 | 11/2006 | Voegele et al. |
| 2006/0247678 | A1 | 11/2006 | Weisenburgh, II et al. |
| 2006/0260616 | A1 | 11/2006 | West et al. |
| 2006/0260617 | A1 | 11/2006 | Abolfathi et al. |
| 2006/0264999 | A1 | 11/2006 | Davison et al. |
| 2006/0270911 | A1 | 11/2006 | Voegele et al. |
| 2006/0271057 | A1 | 11/2006 | Shluzas et al. |
| 2006/0271096 | A1 | 11/2006 | Hamada |
| 2006/0276821 | A1 | 12/2006 | Davison et al. |
| 2006/0276822 | A1 | 12/2006 | Davison et al. |
| 2007/0021768 | A1 | 1/2007 | Nance et al. |
| 2007/0032703 | A1 | 2/2007 | Sankaran et al. |
| 2007/0060939 | A1 | 3/2007 | Lancial et al. |
| 2007/0078436 | A1 | 4/2007 | Leung et al. |
| 2007/0088258 | A1 | 4/2007 | Wenchell et al. |
| 2007/0100366 | A1 | 5/2007 | Dziedzic et al. |

FOREIGN PATENT DOCUMENTS

| | | |
|---|---|---|
| WO | 9819730 A1 | 5/1998 |
| WO | WO 2005122953 A2 * | 12/2005 |
| WO | 2006017507 A2 | 2/2006 |
| WO | 2006094243 A1 | 9/2006 |
| WO | 2007/002392 A2 | 1/2007 |
| WO | 2007/021708 A1 | 2/2007 |

* cited by examiner

SURGICAL SITE ACCESS SYSTEM AND DEPLOYMENT DEVICE FOR SAME

The present application is related to PCT/US2006/024472, entitled "Expandable Surgical Site Access System" filed on Jun. 23, 2006 and "Access Port Expander and Method" filed on even date herewith, each disclosure of which is hereby incorporated herein by reference in its entirety.

FIELD OF THE INVENTION

The present invention relates generally to devices and methods for performing minimally invasive, percutaneous surgeries. More particularly, the present invention relates to a surgical site access system and device for same to deploy the surgical site access system within a body.

BACKGROUND OF THE INVENTION

Traditional surgical procedures often require a long incision, extensive muscle stripping, and prolonged retraction of tissues to access the desired surgical site as well as denervation and devascularization of surrounding tissue. This is particularly the case with spinal applications because of the need for access to locations deep within the body. Such surgical procedures can cause significant trauma to intervening tissues and potential damage to good tissue due to the amount and duration of tissue retraction, resulting in increased recovery time, permanent scarring, and pain that can be more severe than the pain that prompted the original surgical procedure. This is further exacerbated by the need to make a large incision so that the surgeon can properly view the areas inside the body that require attention.

Endoscopic, or minimally invasive, surgical techniques allow a surgical procedure to be performed on a patient's body through a smaller incision in the body and with less body tissue disruption. Endoscopic surgery typically utilizes a tubular structure known as a cannula (or portal) that is inserted into an incision in the body. A typical cannula is a fixed diameter tube, which a surgeon uses to hold the incision open and which serves as a conduit extending between the exterior of the body and the local area inside the body where the surgery is to be performed. Thus, cannulae can be used for visualization, instrument passage, and the like.

The typical cannula, however, presents at least two disadvantages. First, insertion of the cannula typically requires an incision. Although this incision is often relatively smaller than incisions made for surgical procedures performed without a cannula, there is still trauma to healthy tissue. There also may be a need to dilate the tissue prior to insertion of the cannula. Additionally, endoscopic surgical techniques may be limited by the size of the cannula because some surgical instruments, such as steerable surgical instruments used in posterior discectomies, are sometimes larger than the size of the opening defined by the cannula. Therefore, there is a need for a surgical site access system that can be inserted with minimal incision of tissue yet still provide an entrance opening and conduit sized for sufficient instrument passage and operation.

SUMMARY OF THE INVENTION

The present invention overcomes the foregoing and other shortcomings and drawbacks of surgical site access systems heretofore known. While the invention will be described in connection with certain embodiments, it will be understood that the invention is not limited to these embodiments. On the contrary, the invention includes all alternatives, modifications and equivalents as may be included within the spirit and scope of the present invention.

The present invention is directed to a surgical site access system and deployment device for performing minimally invasive, percutaneous surgeries to access the spine or other bone structures, organs or locations of the body. In one embodiment, the surgical site access system comprises an elongated, expandable stent that is particularly adapted to be deployed in a body during a surgical procedure to provide access to a surgical site within the body.

In accordance with one aspect of the present invention, the stent defines a working channel through the body from a point of entry to the surgical site. The working channel defines a passageway through which a surgeon may view the area of interest and pass surgical instruments and/or other devices (not shown) to the surgical site from outside the point of entry by providing a barrier against surrounding tissue, organs, bodily fluids and the like.

In one embodiment, the stent is a self-expanding stent that is configurable from a collapsed first configuration to an expanded second configuration. The stent is delivered to the surgical site in a collapsed state on a distal end of a delivery device. Following deployment, the self-expanding stent expands radially outwardly so as to provide access to the surgical site through the working channel defined by the stent between the point of entry and the surgical site.

In accordance with another aspect of the present invention, the stent comprises an axially compressible stent that is configurable from a first length to a shortened second length upon axial compression of the stent. The stent defines a first diameter at the first length and an expanded second diameter at the shorted second length upon axial compression of the stent. The stent body is operable, in the axially compressed state, to provide a working channel between the point of entry and the surgical site.

In accordance with yet still another aspect of the present invention, the stent comprises an axially compressible stent, a stationary member associated with a proximal end of the stent, a rotatable member supported for rotation relative to the stationary member and a plurality of flexible elongated members operably coupled between the rotatable member and a distal end of the stent. The flexible elongated members axially compress the stent upon rotation of the rotatable member relative to the stationary member. The stent is operable, in the axially compressed state, to provide a working channel between the point of entry and the surgical site.

These and other objects and advantages of the present invention will be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE PREFERRED EMBODIMENTS

Referring now to the figures, and to FIGS. 1, 2 and 3A-3D in particular, an elongated, expandable stent 20 according to one embodiment of the present invention is shown. As will be described in greater detail below, stent 20 is particularly adapted to be deployed into a body 22 and expanded radially outwardly during a surgical procedure to provide access to a surgical site 24, possibly deep within the body, when the stent 20 is deployed and expanded. The stent 20 may be an integral component and is configured to maintain an open passage through soft tissue in the body for providing surgical access to a remote portion of the body during a surgical procedure.

The stent 20 defines a working channel 26 (FIG. 3D) through the body 22 from a point of entry 28 to the surgical site 24. The working channel 26 defines a passageway through which a surgeon may view the area of interest and pass surgical instruments and/or other devices (not shown) to the surgical site 24 from outside the point of entry 28 by providing a barrier against surrounding tissue, organs, bodily fluids and the like. It is understood that a working channel can be provided for any number of surgical procedures. The point of entry 28 may be a percutaneous opening made by piercing a patient's skin 30 with a needle (not shown) or a guide wire 32, by making a small incision in the patient's skin, or by any other minimally invasive approach well known to those skilled in the art.

The stent 20 may be a generally self-expanding stent comprising a mesh, lattice or other structure that has a shape memory configuration so that the stent 20 assumes an expanded, open lumen configuration when the stent 20 is allowed to seek its own natural configuration. In one embodiment, the stent 20 may comprise a set of braided wires 34 made of materials that have shape memory characteristics (for example, PH 17-7 stainless steel wire, plastics, or Nitinol) and that can be set in the desired open, deployed configuration. The wires 34 can be braided into the desired configuration, heat treated, and then compressed for placement onto a delivery device 36 as will be described in detail below. The braid wires provide a desired cover factor and braid angle. The cover factor and braid angle determine the degree of elongation and expansion that the stent 20 can experience around the nominal braid diameter. The braid's nominal geometry prior to setting the shape memory can be obtained by several methods including simple braiding onto a mandrel or combined processes such as braiding onto a mandrel combined with a deformation process to plastically deform the wire braid. It will be appreciated that in other embodiments, the stent 20 may comprise other mesh or non-mesh structures and/or be constructed of other metal or non-metal materials well known to those of ordinary skill in the art without departing from the spirit and scope of the present invention. It will also be appreciated that the stent 20 can be constructed of a material that allows for sequential dilation of the stent. The construction of the stent 20 may vary depending on the surgical procedure being performed, and its characteristics and construction may depend on such factors as the soft tissue, organ and bodily fluid barrier requirements, the desired size and shape of the working channel 26, and the location of the surgical site 24 within the body. It will be further appreciated that the stent 20 can be woven into a desired configuration from a single, or optionally multiple strands, of material.

In one embodiment, the stent 20 may be provided with a membrane (not shown) made of expanded PTFE, polyester fiber, an elastomeric coating or a hydrogel coating. Other biocompatible materials are possible as well. The membrane may be located around the outer perimeter of the stent wall 40 and, in one embodiment, may be finished over the ends of the braided wires 34 so that the wire ends are not exposed. The finishing can be by overmolding material over the wire ends, or by melt processing the material over the wire edges. Melt processing can be accomplished by simply folding material over the wires, placing heat shrink material onto the area to be treated and exposing the heat treat material to a suitable heat source, such as a hot air gun or heated die. Other melt processing methods could include ultrasonic welding or any other suitable method. While not shown, it is contemplated that the membrane may be located on the inside perimeter of the stent wall 40. In yet another embodiment, both an inner and an outer membrane (not shown) may be secured to the stent wall 40 to completely envelope the braided wires 34. The membrane provides a fluid barrier to minimize the inflow of bodily fluids through the wall 40 of the stent 20 and into the working channel 26 during a surgical procedure. It is also contemplated that the stent 20 may not include a membrane so that the wall 40 of the stent 20 directly contacts the surrounding tissue.

Figures 5, 6:
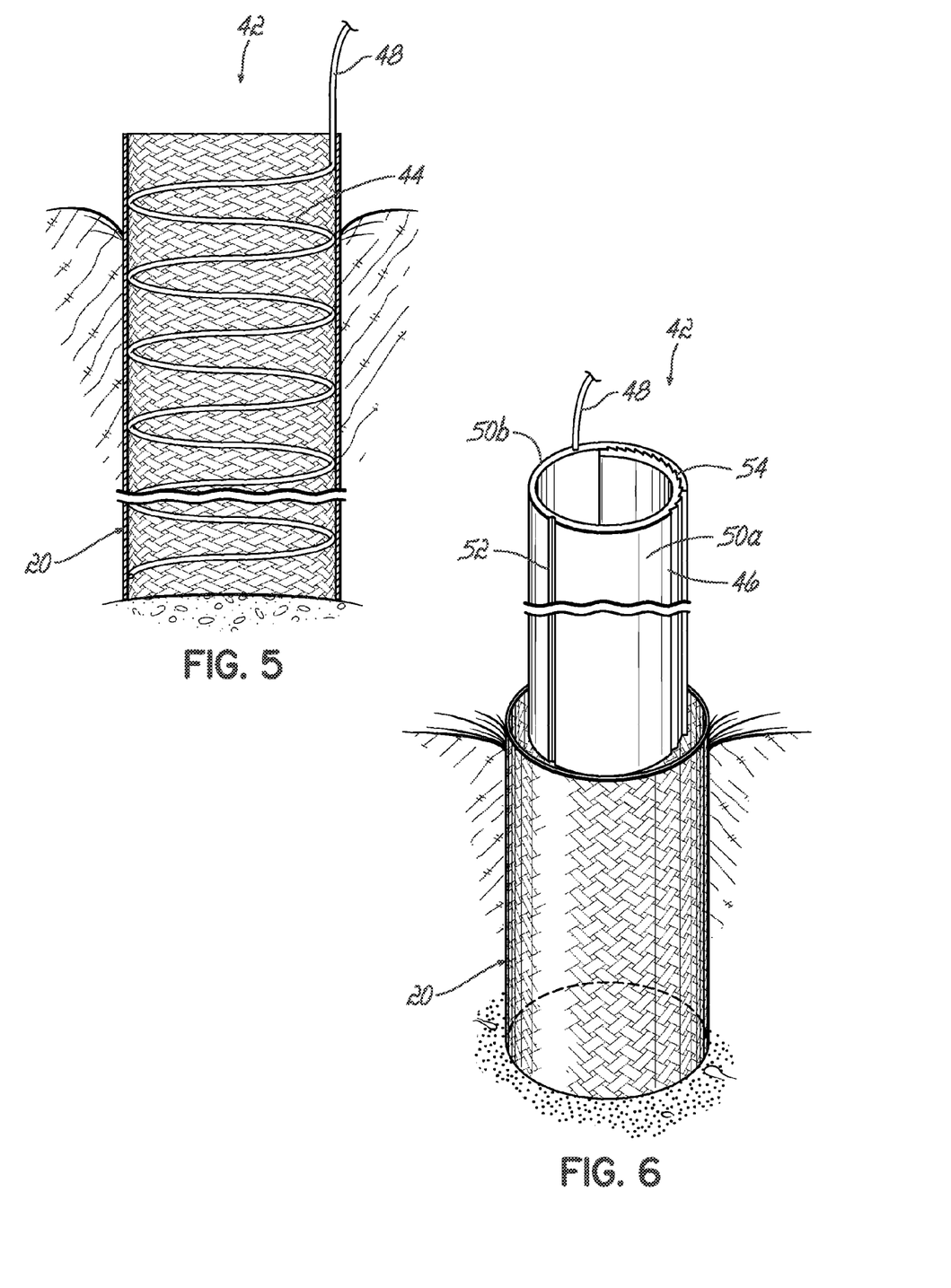
FIG. 5 is a diagrammatic view of an illumination device for illuminating a working channel defined by the stent of FIGS. 1, 2, 3A-3C, 4A and 4B.
FIG. 6 is a view similar to FIG. 5 illustrating an illumination device in accordance with another aspect of the present invention for illuminating a working channel defined by the stent of FIGS. 4A and 4B.

Referring now to FIGS. 5 and 6, the stent 20 may be provided with an illumination system 42 comprising one or more fiber optic rods 44 or a radially expandable tube 46. Other suitable illumination devices are possible as well. The fiber optic rod 44 or tube 46 may be made of any optical quality polymer, glass or other suitable material. The fiber optic rod 44 or tube 46 is coupled to an illuminating source (not shown) through a fiber optic feed 48.

In one embodiment, as shown in FIG. 5, the fiber optic rod 44 comprises a helically wound or spiral rod that is inserted into the stent 20 after it has been radially expanded to illuminate the working channel 26 created by the stent 20. The coiled fiber optic rod 44 may also help support the radial load applied to the stent 20 to maintain the open shape of the working channel 26.

In another embodiment, as shown in FIG. 6, the tube 46 is inserted into the stent 20 and then radially expanded as will be described in greater detail below. The tube 46 is split and includes at least two sections 50a, 50b that are hinged together at hinge 52. Hinge 52 may comprise a living hinge as shown, a pinned hinge (not shown) or any other type of suitable hinge mechanism or other type of flexible connection. The tube 46 may also be sectioned so as to be flexible along its length to permit bending of the tube 46. A rack and pawl mechanism 54 may be provided generally opposite the hinge 52 to permit radial expansion of the tube 46 within the stent 20, and maintain the expanded radial expansion of the tube 46. The expanded tube 46 may also help support the radial load applied to the stent 20 to maintain the open shape of the working channel 26.

The stent 20 of the present invention will now be described in connection with its use during a spinal discectomy procedure as shown in FIGS. 1, 2 and 3A-3D. Stent 20 can also be used in other spinal surgical procedures such as laminectomies, pedicle screw placement, dynamic stabilization system placement, and fusion device placement, and can be used from an anterior, posterior, lateral, posterio-lateral or transforaminal approach. While the present invention will be described herein in connection with spinal surgery, it will be appreciated that the stent 20 of the present invention has broad uses in many varied surgical procedures requiring access through a body to a surgical site and is therefore not limited to spinal surgery.

Figure 1:
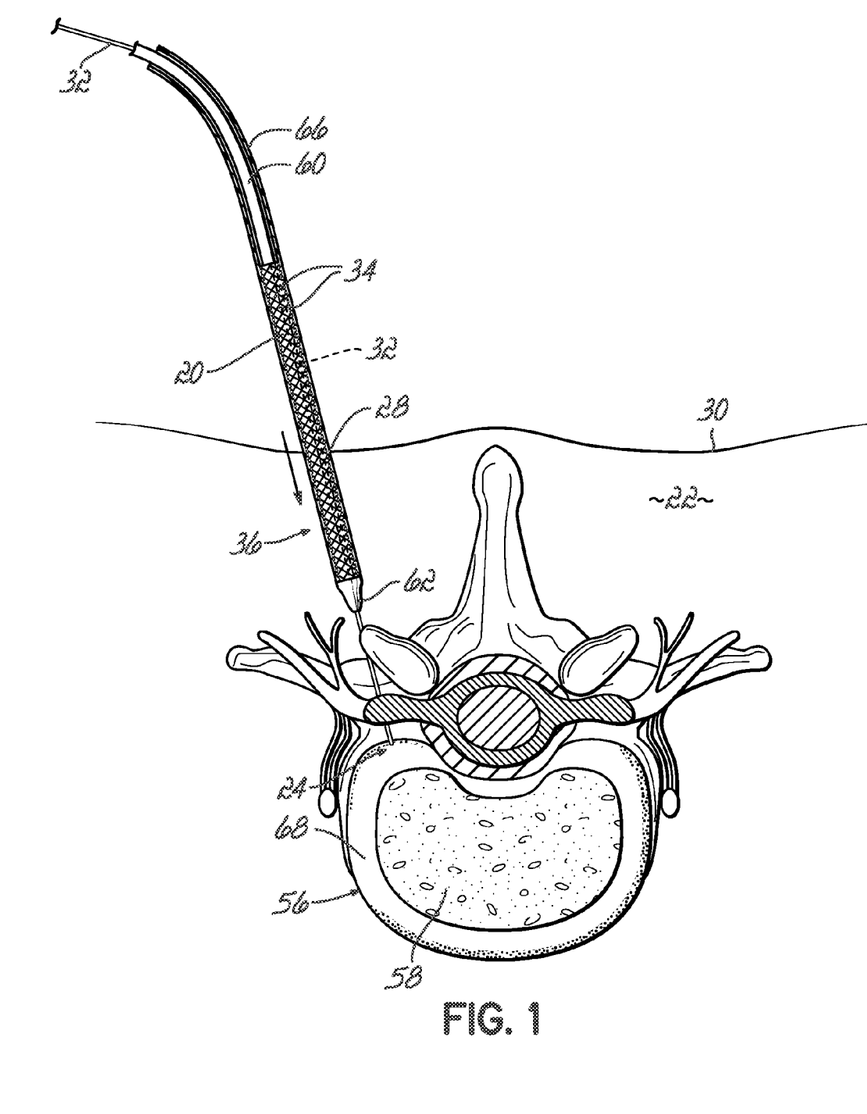
FIGS. 1, 2 and 3A-3D are diagrammatic views illustrating sequential steps for deploying a stent according to one embodiment of the present invention for providing access to a surgical site from a point of entry.

In a first step of the procedure, as shown in FIG. 1, the guide wire 32 can be advanced through the skin 30 and soft tissue to the desired surgical site, such as the intervertebral disc 56. The guide wire 32 may be a line of sight guide wire (k-wire) or a steerable guide wire, such as the Reuter tip deflecting wire guide commercially available from Cook, Inc. The guide wire 32 may be provided with a penetrating tip. The penetrating tip may be made of PH 17-7 stainless steel, polyimide, PEEK, or suitable metals, polymers, or ceramics that allow the penetrating tip to be mated to the guide wire 32.

Figure 2:
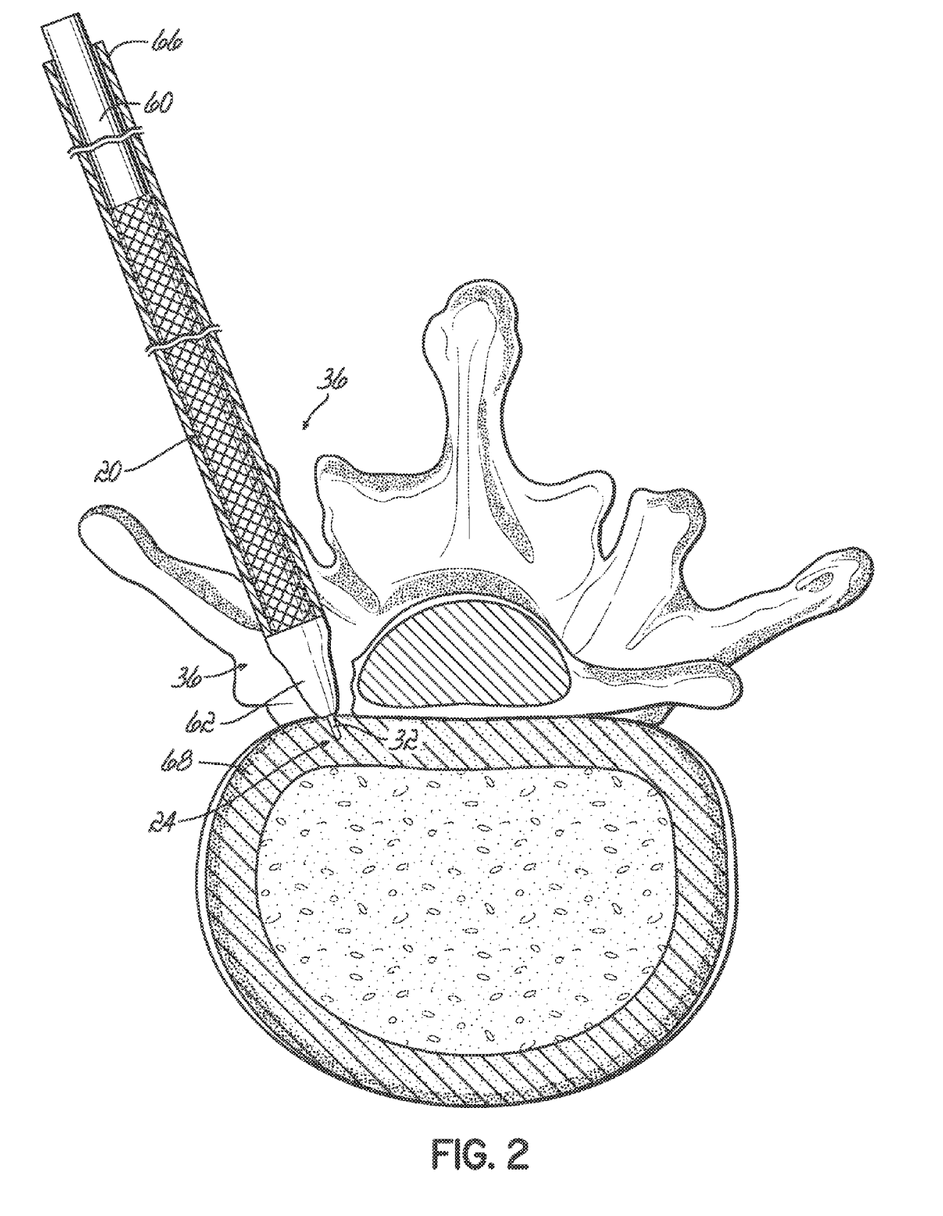

Preferably, a local anesthetic may be administered with an access needle (not shown) and a small incision of about 1 cm in length (the incision length may be varied depending on surgical procedure) is made in the skin 30 and underlying fascia to facilitate penetration of the guide wire 32 through the skin 30. The guide wire 32 may be advanced from the point of entry 28 to the surgical site 24 under fluoroscopy, direct visual guidance or any other suitable guidance method. After the guide wire 32 reaches its target, such as the intervertebral disc 56, the wire 32 may be advanced into the disc space 58 for access location as shown in FIGS. 1 and 2.

Figure 3A:
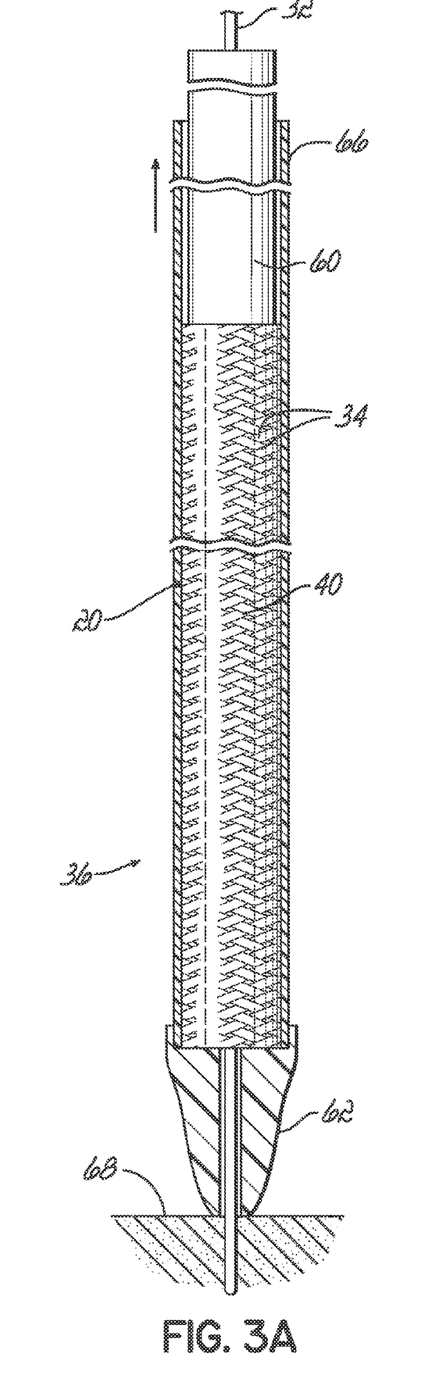
Figure 3B:
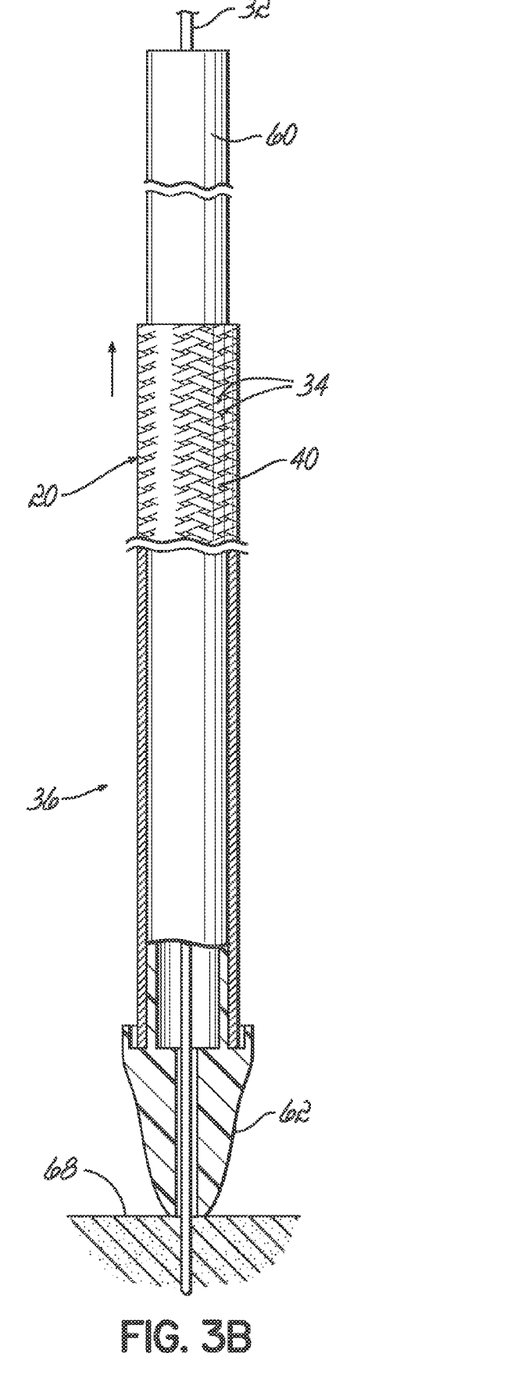

In one aspect of the present invention, as shown in FIGS. 1, 2 and 3A-3D, the stent 20 is releasably mounted on the delivery device 36 which is guided to the surgical site 24 via the guide wire 32. The delivery device 36 may be made of polyesters, polybutylenes, polyamides, elastomers or the like. The delivery device 36 includes an elongated cannulated shaft 60 and a retention tip 62 provided adjacent the distal end of the shaft 60. As used herein, the term "distal" is intended to refer to a location remote from the surgeon while the term "proximal" is intended to refer to a location closer to the surgeon. The retention tip 62 is also cannulated and is provided with an annular recess 64 (FIGS. 3C and 3D) that surrounds the shaft 60. As will be described in greater detail below, the recess 64 is configured to receive a distal end portion of the stent 20 as shown in FIGS. 3A and 3B. The retention tip 62 may be generally conically shaped so that it tapers inwardly from adjacent the annular recess 64 toward a distal end of the retention tip 62.

The stent 20 is collapsed on the shaft 60 of the delivery device 36 and is covered by an elongated retaining sheath 66 that maintains the collapsed state of the stent 20. As shown in FIGS. 3A and 3B, a distal end portion of the retaining sheath 66 is also received within the annular recess 64 of the retention tip 62 so that the stent 20 is captured between the retaining sheath 66 and the shaft 60 of the delivery device 36. The delivery device 36 and the stent 20 are advanced along the guide wire 32 to the surgical site 24 where the stent 20 is to be deployed. The retaining sheath 66 is a retractable or removable sheath that holds the stent 20 in a compressed configuration until the sheath 66 is moved or retracted off of the stent 20 so that the stent 20 is no longer radially constrained and is released from the delivery device 36. The retaining sheath 66 can be simply retracted by sliding or rolling, or it can be configured for tear away removal. The sheath 66 may comprise a membrane that is provided with perforations or a scoring mark to assist in making a preferential tear. A wire or other suitable device may be provided in or on the membrane to assist in making the preferential tear. In one embodiment, the stent 20 may have an outer diameter in its compressed state of between about 3 mm and about 12 mm, although other outer diameters are possible as well for the stent 20 depending on the working channel requirements for a particular surgical procedure.

Figure 3C:
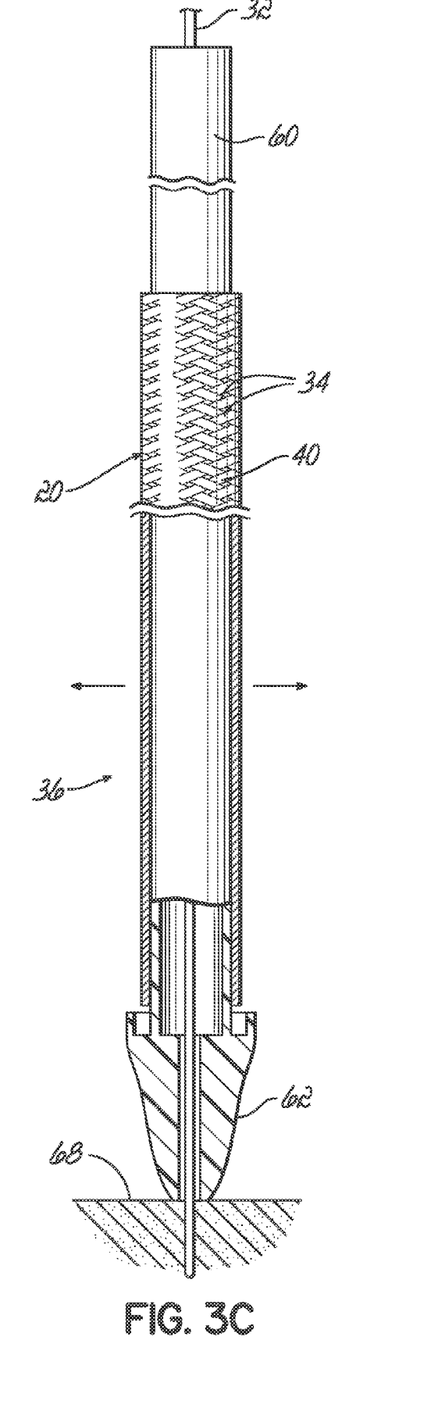
Figure 3D:
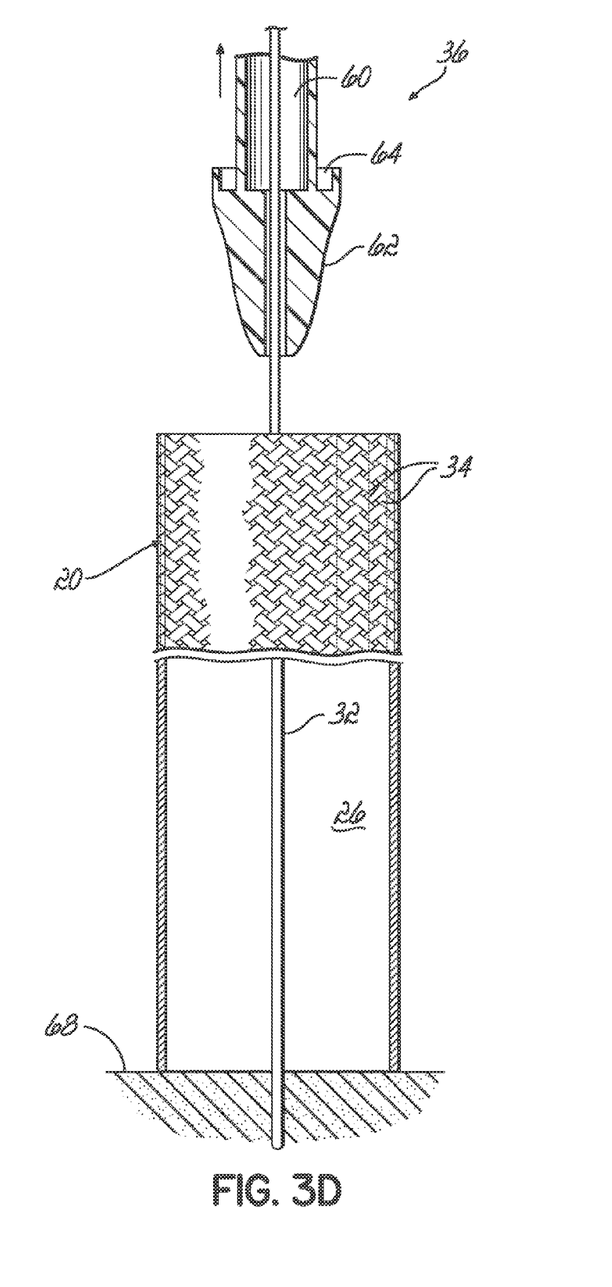

As shown in FIGS. 3C and 3D, when the retaining sheath 66 is removed, the distal end portion of the stent 20 is released from the annular recess 64 of the retention tip 62 so that the stent 20 is free to assume its preferred radially expanded configuration. The stent 20 is deployed at the surgical site 24 and extends from outside of the point of entry 28 to the annulus 68 of the intervertebral disc 56. The deployed stent 20 expands from its compressed state outwardly to a greater first cross-sectional extent. In its deployed state, the stent 20 is configured to resist inward pressure from soft tissue, organs and bodily fluids to maintain the open working channel 26 from the point of entry 28 to the surgical site 24. In one embodiment, in which the stent 20 has a cylindrical cross-sectional profile, the stent 20 may expand in diameter between about 1 mm and 3 mm beyond the compressed outer diameter of the stent 20 when the stent 20 is released from its compressed state. In other embodiments, the stent 20 may expand to a greater or lesser cross-sectional extent when it is released from the delivery device 36. The amount of expansion of the deployed self-expanding stent 20 will depend on the particular configuration of the stent 20 and other anatomical factors present during the surgical procedure.

Following deployment of the stent 20 at the surgical site 24, a balloon (not shown) may be advanced along the guide wire 32 and inserted into the expanded stent 20 as fully described in PCT/US2006/024472 and previously incorporated herein by reference. The balloon may be inserted into the stent 20 without guidance along the guide wire 32. The balloon is connected in a known manner to a fluid source so that the balloon may be expanded outwardly to thereby expand the stent 20 radially outwardly to the desired radial extent. The amount of expansion of the stent 20 will depend on the configuration of the stent 20, the configuration and operation of the dilation balloon and the desired size and shape of the working channel 26 defined by the expanded stent 20. In one embodiment, in which the stent 20 has a cylindrical cross-sectional profile, the stent 20 may expand in diameter to about 24 mm, although other expanded diameters of the stent 20 are possible as well. The balloon can be expanded to a desired atmospheric pressure so that the pressure can be kept below a level that causes tissue injury. Additionally, the inflation of the balloon, and hence the expansion of the stent 20, may be generally continuous and the rate of expansion controlled to minimize further tissue injury during the deployment of the stent 20.

The balloon (not shown) is removed following expansion of the stent 20. The expanded stent 20 defines the working channel 26 extending from the point of entry 28 to the surgical site 24. The guide wire 32 may be left in place within the working channel 26 so that devices such as cannulated drills, reamers, and screws and the like can be advanced to the distal end of the stent 20 and/or along the guide wire 32 to the surgical site 24. For example, a surgeon could first pass fusion instruments through the stent to prepare a surgical site for receipt of a fusion implant and fusion mounting material, such as a cage, bone graft or other suitable fusion implant or material. This procedure can then be followed by passing pedicle screw assemblies through the stent and attaching them to the spine. Alternatively, a dynamic stabilization system like the Dynesys® system, available from Zimmer Spine, can be passed through the stent and assembled at the spine of the patient. Following the surgical procedure, the stent 20 may be at least partially collapsed by grasping the proximal end of the stent 20 by hand or by instrument and withdrawing the stent 20 from the point of entry 28.

When the radially expandable tube 46, as shown in FIG. 6, is used as an illumination system, the tube 46 is inserted into the expanded stent 20. The balloon (not shown) is then inserted into the tube 46 and is reinflated to radially expand the tube 46 so that the tube 46 engages the wall 40 of the stent 20. The rack and pawl mechanism 54 permits radial expansion of the tube 46 within the stent 20, and maintains the expanded radial expansion of the tube 46.

Alternatively, by way of example, the stent 20 may be radially expanded by use of the access port expander as fully described in "Access Port Expander and Method" Ser. No. 11/778,123 and previously incorporated herein by reference. It will be appreciated that other methods for radially expanding the stent 20 are possible as well such as manual manipulation of the stent 20 by the surgeon.

The stent 20 may be constructed to be flexible along at least a portion of its length to accommodate a curved trajectory to the surgical site and/or manipulation of the stent 20 by a surgeon during a procedure. In its deployed and expanded state, the stent 20 may define a working channel 26 that is curved along at least a partial length of the stent 20. The expanded cross-sectional profile of the stent 20 need not be cylindrical. The curvature and various cross-sectional shapes obtainable with the stent 20 are variable and selectable by the surgeon depending on the configuration of the stent 20, the requirements for a particular surgical procedure and the configuration of the balloon(s) used to expand the stent outwardly.

Figure 4A:
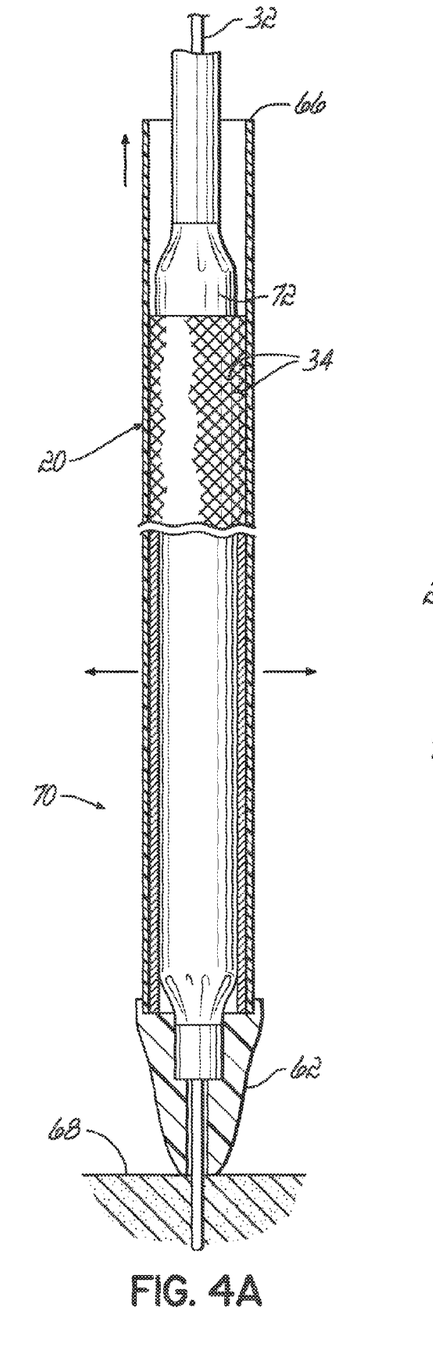
FIGS. 4A and 4B are diagrammatic views illustrating sequential steps for deploying a stent according to another aspect of the present invention.
Figure 4B:
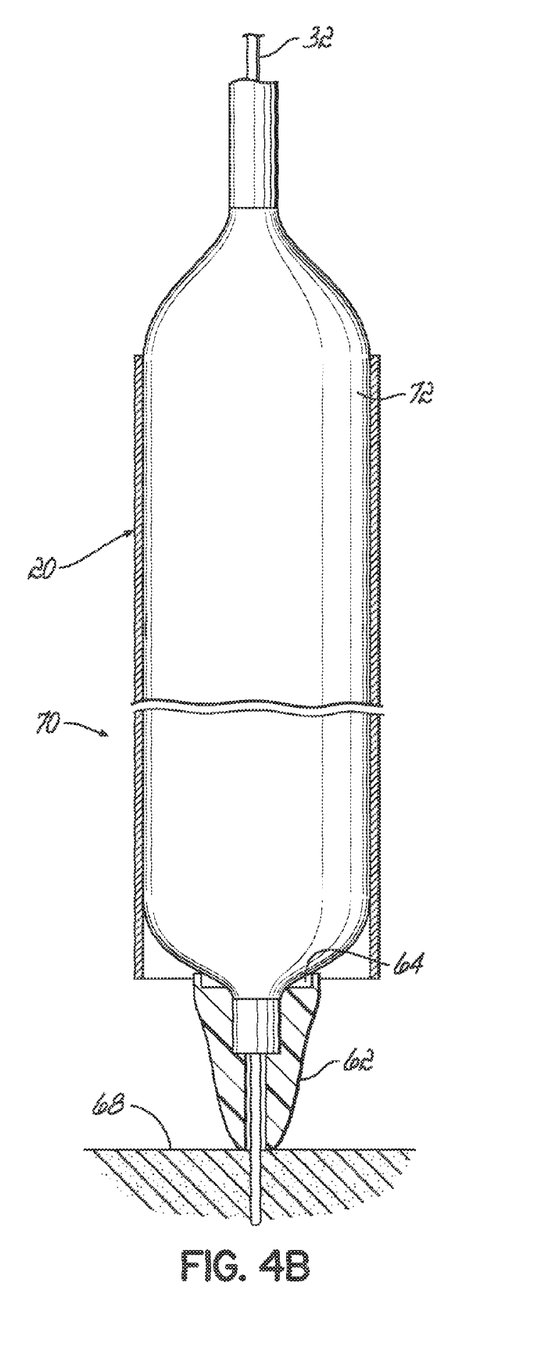

According to another aspect of the present invention, as shown in FIGS. 4A and 4B, an alternative delivery device 70 is provided for delivering the stent 20 to the surgical site 24 and radially expanding the stent 20 at the site 24, where like numeral represent like parts to the delivery device 36 shown and described in connection with FIGS. 1, 2 and 3A-3C. The delivery device 70 includes a dilation balloon 72 and a retention tip 62 provided adjacent the distal end of the balloon 72. As described above, the retention tip 62 is provided with the annular recess 64 to receive the distal end portion of the stent 20.

The stent 20 is collapsed on the balloon 72 of the delivery device 70 and is covered by the elongated retaining sheath 66 that maintains the collapsed state of the stent 20. As shown in FIG. 4A, a distal end portion of the retaining sheath 66 is also received within the annular recess 64 of the retention tip 62 so that the stent 20 is captured between the retaining sheath 66 and the balloon 72 of the delivery device 70. The delivery device 70 and the stent 20 are advanced along the guide wire 32 to the surgical site 24 where the stent 20 is to be deployed.

The retractable sheath 66 is then removed so that the stent 20 is released from the annular recess 64 and the stent 20 is free to assume its radially expanded configuration. The balloon 72 is then inflated as shown in FIG. 4B to expand the stent 20 radially outwardly to the desired radial extent.

The balloon 72 is then removed following expansion of the stent 20 so that the expanded stent 20 defines the working channel 26 extending from the point of entry 28 to the surgical site 24. As described above, the guide wire 32 may be left in place within the working channel 26 so that devices such as cannulated drills, reamers, and screws and the like can be advanced along the guide wire 32 to the surgical site 24. Following the surgical procedure, the stent 20 may be at least partially collapsed by grasping the proximal end of the stent 20 by hand or by instrument and withdrawing the stent 20 from the point of entry 28.

Referring now to FIGS. 7, 8, 9A and 9B, a stent 100 and stent delivery system 102 according to another aspect of the present invention are shown. In this embodiment, the stent 100 is configured to be axially compressible so that in its initial deployed state (FIG. 10A), the stent 100 has a first length and a first diameter of $D_1$. Following initial deployment of the stent 100 using the stent delivery system 102, the stent 100 is subjected to an axially compressive force so that the stent 100 is axially compressed as shown in FIG. 10B. In its axially compressed state, the stent 100 has a shortened second length and a radially expanded second diameter $D_2$ so that the stent 100 defines a working channel 104 (FIG. 10B) through the body 22 from the point of entry 28 to the surgical site 24. The distal end portion 106 of the stent 100 is configured to intimately mate with a patient's bony structure, such as portions of the patient's spine, when the stent 100 is axially compressed following its deployment.

In one embodiment, the stent 100 may comprise a bi-axial braid, lattice, mesh or other suitable structure which is configured to expand radially when the stent 100 is subjected to an axially compressive force. In other embodiments, the stent 100 has a woven configuration. For example, the stent 100 may comprise a set of bi-axially braided wires or flat wires made of Nitinol, stainless steel or polymeric materials, such as braided and woven structures. Other suitable metal and non-metal materials are possible as well as will be appreciated by those of ordinary skill in the art. In one embodiment, a single strand of Nitinol material forms the stent and exerts constant radial pressure which minimizes traumatic tissue compression. While not shown, it will be appreciated that the stent 100 may be provided with a membrane made of expanded PFTE, polyester fiber, an elastomeric coating or a hydrogel coating as described in detail above. The membrane (not shown) provides a fluid barrier to minimize the inflow of bodily fluids through the wall 108 of the stent 100 and into the working channel 104 during a surgical procedure.

Further referring to FIGS. 7, 8, 9A and 9B, the stent delivery system 102 includes, in one embodiment, a mandrel 110 having an elongated cannulated shaft 112 and a retention tip 114 provided adjacent a distal end of the shaft 112. The retention tip 114 is also cannulated and is provided with an annular recess 11 6 (FIGS. 9A and 9B) that surrounds the shaft 112. As will be described in detail below, the recess 116 is configured to receive the distal end portion 106 of the stent 100 as shown in FIGS. 7, 8, 9A and 9B. The retention tip 114 may be generally conically shaped so that it tapers inwardly from adjacent the annular recess 116 toward a distal end of the retention tip 114.

Figure 7:
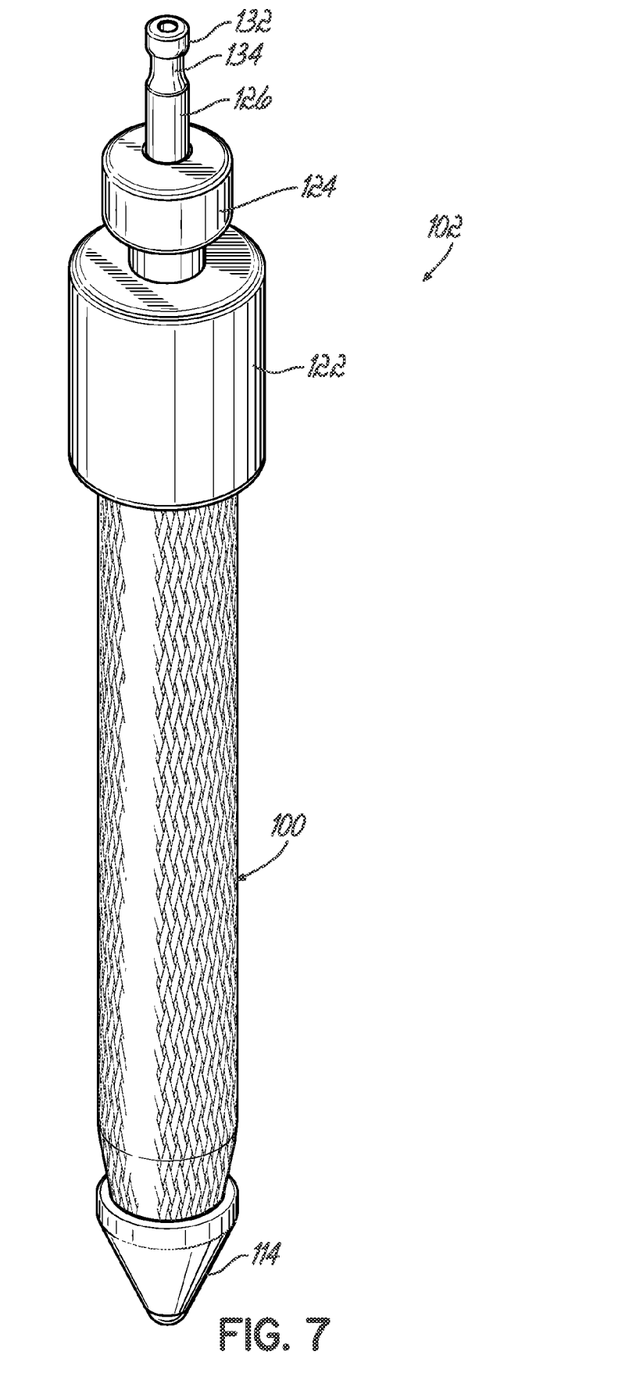
FIGS. 7 and 8 are perspective views of a stent and stent delivery system according to another aspect of the present invention.
Figure 8:
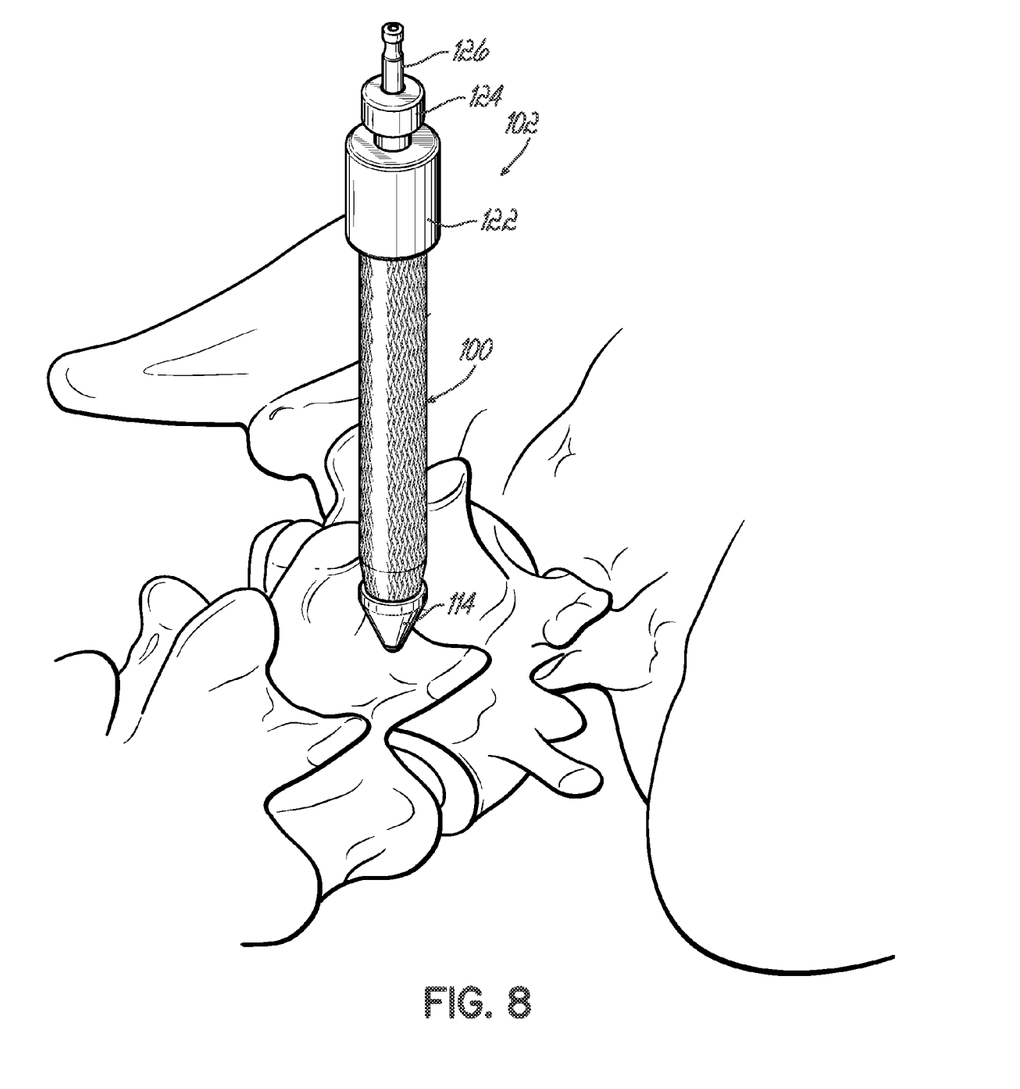
Figure 9A:
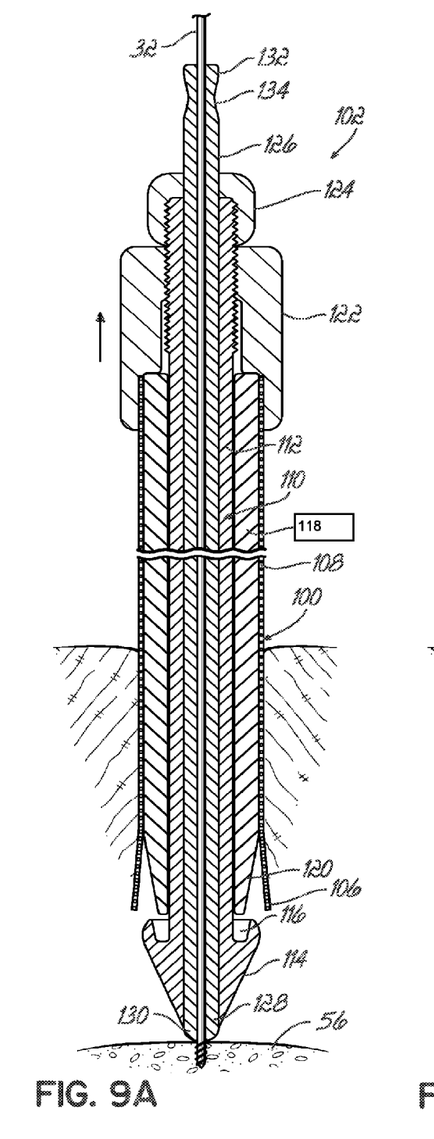
FIGS. 9A and 9B are diagrammatic views illustrating sequential steps for deploying the stent using the stent delivery system shown in FIGS. 7 and 8.
Figure 9B:
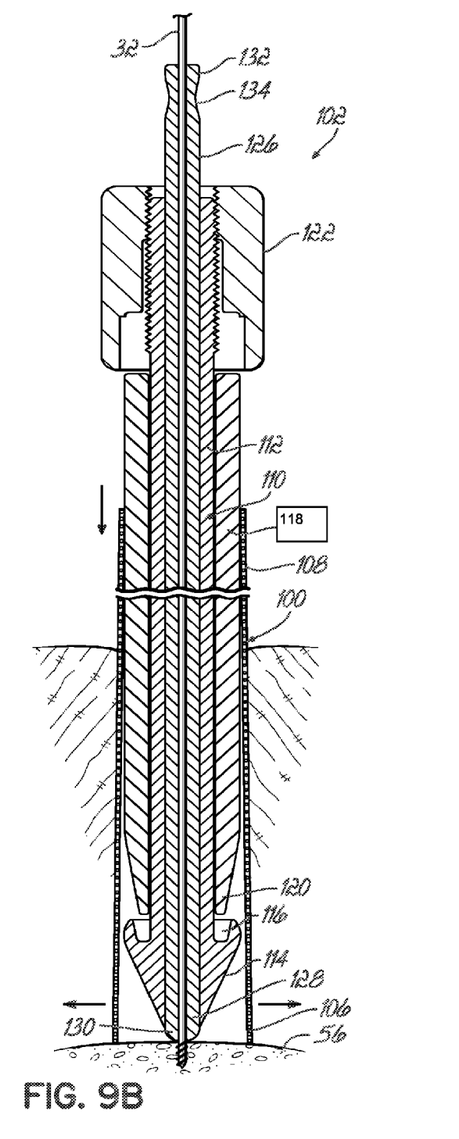

As shown in FIGS. 9A and 9B, the stent delivery system 102 includes a sleeve 118 that is slidably mounted on the mandrel 110 and is sized to be located within the stent 100. A tapered distal end portion 120 of the sleeve 118 is received in the annular recess 116 of the retention tip 114 so as to capture and retain the distal end portion 106 of the stent 100 within the annular recess 116. To this end, a locking knob 122 is threadably mounted on the elongated shaft 112 of the mandrel 110 and is tightened so that the distal end portion 120 of the sleeve 118 tightly engages the distal end portion 106 of the stent 100 within the annular recess 116. An additional locking nut 124 may be threadably mounted on the elongated shaft 112 to retain the locking knob 122 in its tightened position during initial deployment of the stent 100 as shown in FIGS. 7, 8 and 9A. The stent delivery system 102 may be made of polyesters, polybutylenes, polyamides, elastomers or any other suitable material.

As shown in FIGS. 9A and 9B, the stent delivery system 102 includes a sleeve 118 that is slidably mounted on the mandrel 110 and is sized to be located within the stent 100. A tapered distal end portion 120 of the sleeve 100 is received in the annular recess 116 of the retention tip 114 so as to capture and retain the distal end portion 100 of the stent 100 within the annular recess 116. To this end, a locking knob 122 is threadably mounted on the elongated shaft 112 of the mandrel 110 and is tightened so that the distal end portion 120 of the sleeve 118 tightly engages the distal end portion 106 of the stent 100 within the annular recess 116. An additional locking nut 124 may be threadably mounted on the elongated shaft 112 to retain the locking knob 122 in its tightened position during initial deployment of the stent 100 as shown in FIGS. 7, 8 and 9A. The stent delivery system 102 may be made of polyesters, polybutylenes, polyamides, elastomers or any other suitable material.

The stent 100 of the present invention will now be described in connection with its use during a spinal discectomy procedure as shown in FIG. 8. While the present invention will be described herein in connection with spinal surgery, it will be appreciated that the stent 100 of the present invention has broad uses in many varied surgical procedures requiring access through a body to a surgical site and is therefore not limited to spinal surgery per se.

In a first step of the procedure, as shown in FIGS. 9A and 9B, a guide wire 32 (such as a k-wire) can be advanced through the skin and soft tissue to the desired surgical site, such as the intervertebral disc 56 as described in detail above.

An elongated, cannulated retractor 126 is then inserted through the incision site 28 and advanced to the surgical site 24 along the guide wire 32. Alternatively, the retractor 126 may be inserted through the incision site 28 without the use of the guide wire 32. The retractor 126 is configured to create an opening through the tissue between the incision site 28 and the surgical site 24 by splitting and stretching the tissue as opposed to cutting the tissue. The distal end portion 128 of the retractor 126 includes a tapered region 130 to facilitate insertion of the retractor 126 through the tissue. A proximal end portion 132 of the retractor 126 may be provided with an annular notch or recess 134 to facilitate gripping of the retractor 126 by a surgeon's fingers to insert and retract the retractor 126 through the incision site 28.

Figure 10A:
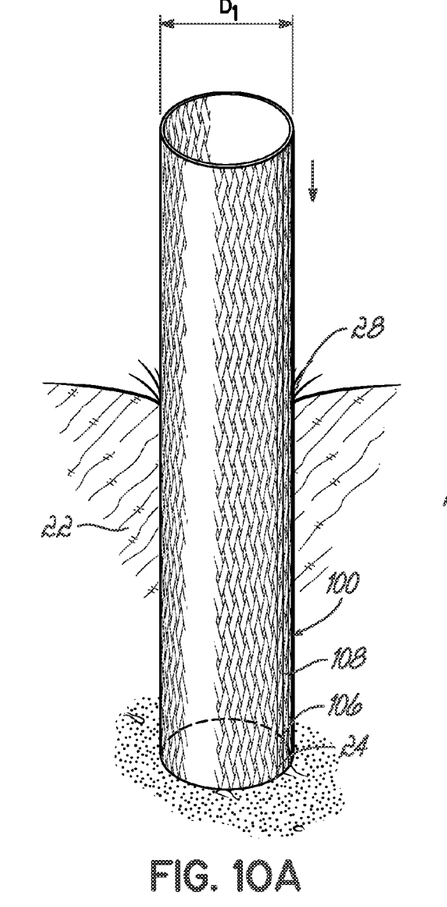
FIG. 10A is a perspective view showing the stent of 9A and 9B in a deployed state.
Figure 10B:
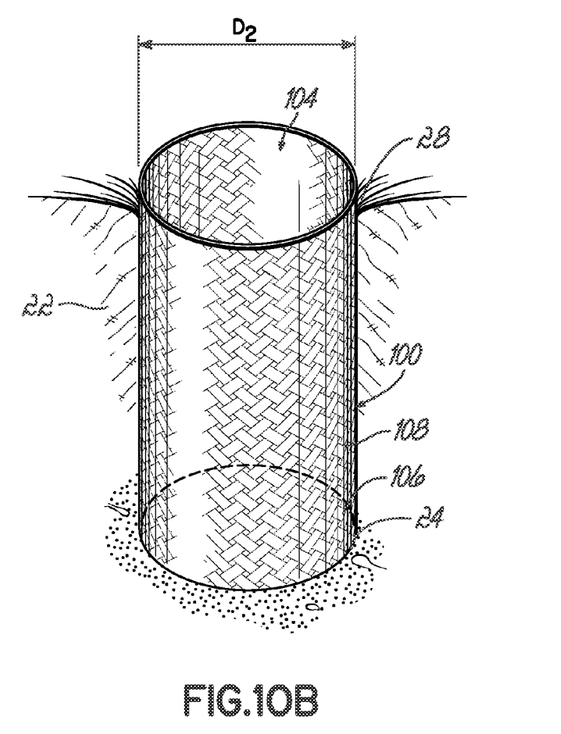
FIG. 10B is a view similar to FIG. 10A, showing the stent in an axially compressed state.

The stent delivery system 102, with the stent 100 supported thereby as shown in FIG. 7 and 8, is then advanced over the retractor 126 until the retention tip 114 of the mandrel 110 is located at or near the desired surgical site 24 as shown in FIG. 8. At this position, the retractor 126 may be removed and the stent 100 is deployed by removing the locking nut 124 and locking knob 122 from the shaft 112 of the mandrel 110 and sliding the sleeve 118 toward the proximal end of the mandrel 110 as shown in FIG. 9A. When the distal end portion 120 of the sleeve 118 generally clears the annular recess 116 of the retention tip 114, the distal end portion 106 of the stent 100 is released as shown in FIGS. 9A and 9B. This allows the stent delivery system 102 to be removed from within the stent 100 as shown in FIG. 10A so that the stent 100 extends from the surgical site 24 to the incision site 28.

Following deployment of the stent 100, the stent 100 is subjected to an axially compressive force, such as by hand or any suitable mechanical structure, so that the stent 100 shortens in length and simultaneously radially expands to define the working channel 104 between the surgical site 24 and the incision site 28 as shown in FIG. 10B. To accommodate the shortening in length, the stent 100 is sized to extend above the incision site 28 prior to expansion, as shown in FIGS. 10A and 10B. The diameter of the working channel 104 generally correlates to the amount of axial force applied to the stent 100.

Figure 11:
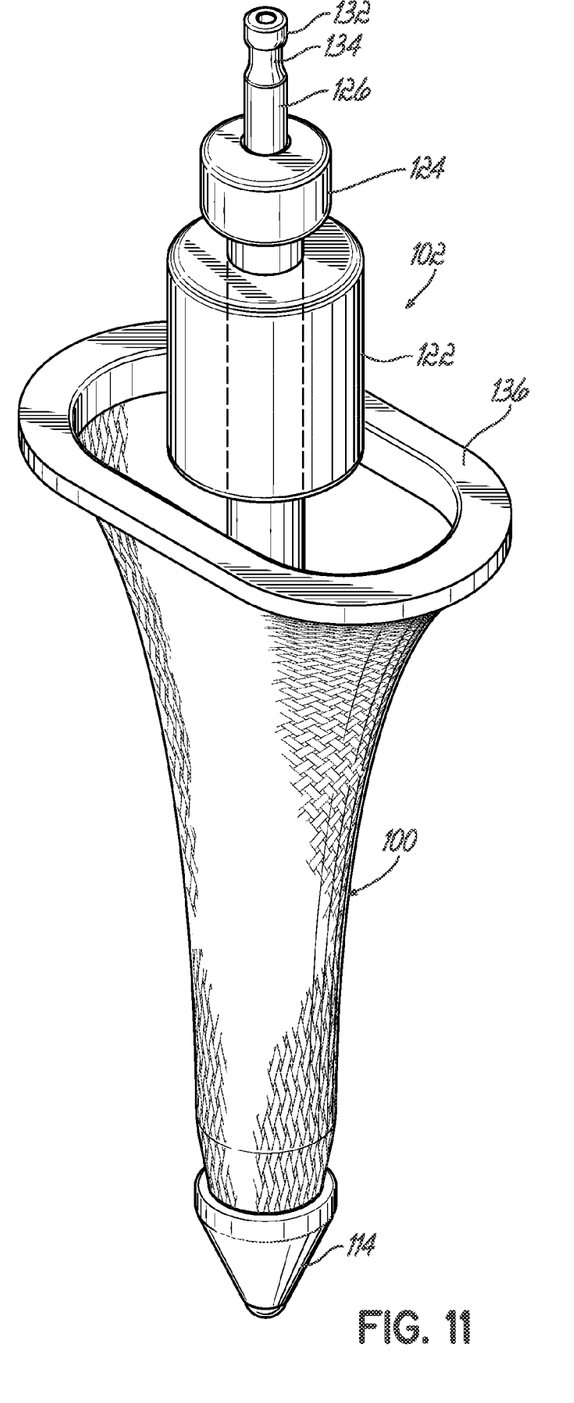
FIG. 11 is a perspective view of a stent according to yet another aspect of the present invention.

In one embodiment, as shown in FIG. 11, a generally rigid access member 136 may be coupled, molded or otherwise joined to the proximal end of the stent 100. In one embodiment, access member 136 has an oval ring shape. In other embodiments, other shapes can be used. The access member 136 may be continuous so as to define a fixed opening of the working channel 104 at the proximal end of the stent 100. The ring member 136 may be attached to a mounting arm or other structure (not shown) that is configured to apply an axially compressive force to the stent 100 to radially expand the stent 100 as shown in FIG. 10B.

In another embodiment, stent 100 of FIG. 11 can be provided without a stent delivery system 102 and can be manually manipulated to expand and provide access to the surgical site. In this embodiment, the access member 136 can be taped with an adhesive surgical pad to the skin of the patient to hold the member 136 in place and to maintain the stent 100 in the expanded configuration. In this configuration, pressure on the distal end of the stent 100 at the surgical site and the maintenance of the access member 136 at the incision with the surgical tape creates the radial expansion.

In another embodiment, the access member 136 can be provided with an adhesive on the surface touching the patient's skin.

Figures 12A, 12B:
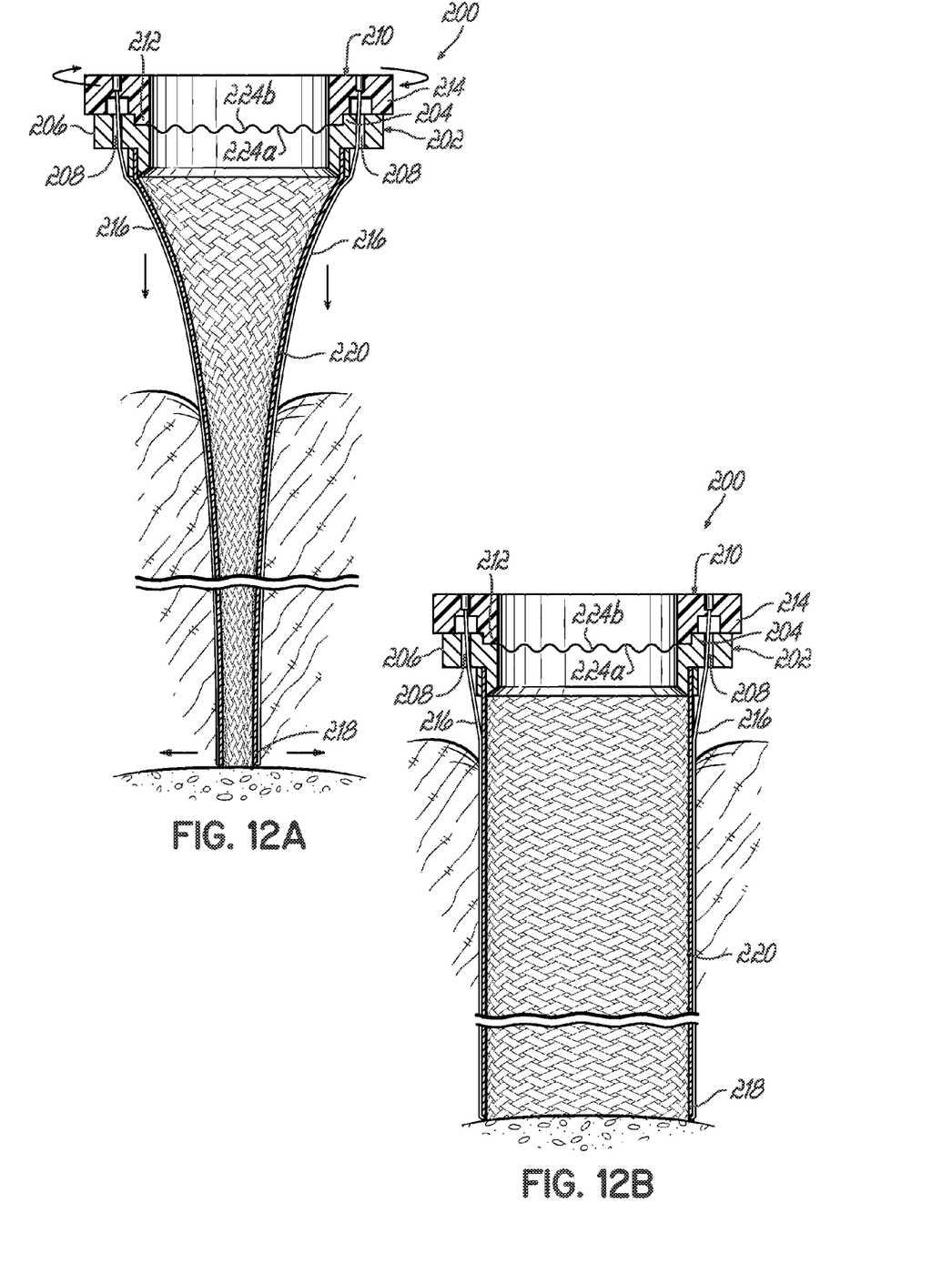
FIGS. 12A and 12B are perspective views of a stent according to another aspect of the present invention.

Referring now to FIGS. 12A and 12B, a stent 200 according to another embodiment of the present invention is shown. In this embodiment, the stent 200 may comprise a bi-axial braid, lattice, mesh, woven or other suitable structure which is configured to expand radially when the stent 200 is subjected to an axially compressive force, similar to the stent 100 of FIGS. 7, 8, 9A and 9B.

A fixed member 202 is coupled, molded or otherwise joined to the proximal end of the stent 200. The fixed member 202 may have many different cross-sectional shapes and includes, in one embodiment, an annular inner shoulder portion 204 and a radially outwardly directed flange portion 206. The flange portion 206 includes a plurality of bores 208 extending therethrough as shown in FIGS. 12A and 12B.

A rotary member 210 is mounted for rotation relative to the fixed member 202 so that a portion 212 of the rotary member 210 sits within the annular inner shoulder 204 of the fixed member 202 and another portion 214 of the rotary member 210 engages the flange portion 206 of the fixed member 202. It will be appreciated that many other types of mounting of the rotary member 210 and fixed member 202 are possible as well without departing from the spirit and scope of the present invention.

In this embodiment of the stent 200, a plurality of elongated flexible members 216, such as wires, cords, cables or other suitable structures, are operatively coupled between the rotary member 210 and the distal end 218 of the stent 200. The flexible members 216 may be incorporated into the wall 220 of the stent 200 or, alternatively, may be located within and/or outside of the stent wall 220. In one embodiment, the flexible members 216 extend through the plurality of bores 208 formed in the flange portion 206 of the fixed member 202 as shown in FIGS. 12A and 12B.

Following deployment of the stent 200, such as by the stent delivery system 102 as described in detail above, the rotary member 210 is rotated relative to the fixed member 202 so that the flexible members 216 are wound upon the rotary member 210. During this rotation, the respective lengths of the flexible members 216 shorten so that the stent 200 is subjected to an axially compressive force as shown in FIG. 12B. In its axially compressed state, the stent 200 has a shortened length and a radially expanded diameter so that the stent 200 defines a working channel 222 through the body 22 from the point of entry 28 to the surgical site 24.

Each of the fixed member 202 and rotary member 210 may be provided with cooperating locking structures 224a, 224b, respectively, so that the rotary member 210 is releasably lockable in a plurality of different rotated positions relative to the fixed member 202. In this way, the rotary member 210 may be indexed and releasably locked to a plurality of different rotated positions relative to the fixed member 202, with each of the different indexed position corresponding to a different diameter of the working channel 222 (e.g. a 180° rotation correlates to an 8 mm diameter working channel).

In another embodiment, the stent can include one or more elongated strands of material that extend along the length of the stent from its distal to proximal end. The strand can extend beyond the proximal end and allow a surgeon to grab the strand and pull the distal end toward the proximal end of the stent forcing the stent into its expanded state. This embodiment of the stent can include an access member, like access member 136 of FIG. 11, that includes a hole that allows the elongated strand to pass through the access member. The strand and hole can be configured to include an interlocking mechanism that maintains the relative positions of the proximal and distal ends of the stent as the strand is pulled by the surgeon and maintains the expansion of the stent.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

What is claimed is:

1. A method for deploying a stent to provide access to a surgical site from a point of entry, comprising:
   providing a stent having a proximal end and a distal end, the stent being expandable from a collapsed first configuration to an expanded second configuration;
   providing a stent delivery system having:
      an elongated cannulated retractor;
      a mandrel having an elongated cannulated shaft surrounding the elongated cannulated retractor;
      a cannulated retention tip provided adjacent a distal end of the elongated cannulated shaft, said cannulated retention tip having an annular recess that surrounds the elongated cannulated shaft;
      a sleeve with a tapered distal end slidably mounted on the mandrel;
      a locking knob threadably mounted on the elongated cannulated shaft of the mandrel which when tightened a distal end portion of the sleeve engages a distal end portion of the stent within the annular recess of the cannulated retention tip to provide the stent in the collapsed first configuration;
      a locking nut threadably mounted on the mandrel to retain the locking knob;
   making an incision at a point of entry;
   creating an access passage through tissue from the point of entry to a surgical site;
   passing the stent in its collapsed first configuration through the access passage created through the tissue along the stent delivery system, wherein the stent is configured to extend from the point of entry to the surgical site;
   removing the retractor;
   removing the locking nut and the locking knob;
   sliding the sleeve toward a proximal end of the mandrel until the distal end portion of the sleeve clears the annular recess of the retention tip releasing the distal end portion of the stent;
   removing the remaining stent delivery system;
   applying an axially compressive force to the proximal end of the stent to cause the stent to expand to the expanded second configuration, wherein in the expanded second configuration the stent expands the passage and defines an open working channel from the point of entry to the surgical site, wherein the surgical site is viewable through the passage.

2. The method of claim 1, further comprising the step of securing the proximal end of the stent to a patient's skin to maintain the stent in its expanded second configuration.

3. The method of claim 1, wherein the step of creating the access passage includes inserting a guide wire through the incision to the surgical site, wherein the stent is passed over the guide wire to the surgical site.

4. The method of claim 1, wherein the step of providing the stent includes providing a self-expanding stent disposed in the collapsed first configuration on a delivery device surrounded by a retaining sheath that maintains the collapsed configuration of the stent.

5. The method of claim 4, wherein the step of applying the force to the proximal end of the stent to cause the stent to expand includes removing the retaining sheath and allowing the stent to self-expand to the expanded second configuration.

6. The method of claim 1, further comprising inserting a balloon into the expanded stent and inflating the balloon to further expand the stent.

7. The method of claim 1, wherein the stent is flexible along at least a portion of its length and the step of creating the access passage includes creating a curved access passage, wherein in the expanded second configuration the stent defines a curved working channel.

8. The method of claim 1, wherein the step of applying the axially compressive force to the proximal end of the stent causes the stent to shorten in length and radially expand.

9. The method of claim 1, further comprising a fixed member coupled to the proximal end of the stent and a rotary member mounted for rotation relative to the fixed member, wherein the step of applying the force to the proximal end of the stent to cause the stent to expand includes rotating the rotary member relative to the fixed member.

10. The method of claim 9, further comprising a plurality of elongated flexible members coupled between the rotary member and the distal end of the stent, wherein rotation of the rotary member shortens the flexible members thereby compressing and radially expanding the stent.

11. The method of claim 10, further comprising a locking member that releasably locks the rotary member in a plurality of rotated positions relative to the fixed member, such that the stent may be expanded and locked in a plurality of positions with corresponding different diameters of the working channel.

* * * * *